United States Patent [19]
Hamper et al.

[11] Patent Number: 5,866,723
[45] Date of Patent: *Feb. 2, 1999

[54] BENZOYL DERIVATIVES AND SYNTHESIS THEREOF

[75] Inventors: Bruce C. Hamper, Kirkwood; Kindrick L. Leschinsky, Ellisville, both of Mo.

[73] Assignee: Monsanto Company, St. Louis, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 671,420

[22] Filed: Jun. 27, 1996

Related U.S. Application Data

[63] Continuation of Ser. No. 277,725, Jul. 20, 1994, Pat. No. 5,532,416, which is a continuation-in-part of Ser. No. 169,285, Dec. 20, 1993, Pat. No. 5,536,700, which is a continuation of Ser. No. 763,762, Sep. 25, 1991, Pat. No. 5,281,571.

[51] Int. Cl.$^6$ .................................................. C07C 49/697
[52] U.S. Cl. ........................... 568/335; 568/336; 568/425; 568/442; 562/474
[58] Field of Search ........................... 562/474; 568/335, 568/336, 425, 442

[56] References Cited

U.S. PATENT DOCUMENTS

| | | | |
|---|---|---|---|
| 2,578,654 | 12/1951 | Hearne et al. | 260/524 |
| 2,695,318 | 11/1954 | Thiel et al. | 260/611 |
| 2,937,209 | 5/1960 | Studer et al. | 260/649 |
| 3,326,662 | 6/1967 | Toyosato et al. | 71/2.5 |
| 3,395,125 | 7/1968 | Moyer | 260/67 |
| 3,426,035 | 2/1969 | Bremmer | 260/297 |
| 3,660,411 | 5/1972 | Levy et al. | 260/293.81 |
| 3,733,321 | 5/1973 | Krapcho | 260/243 |
| 3,832,403 | 8/1974 | Farona et al. | 260/592 |
| 3,948,937 | 4/1976 | Johnson et al. | 260/311 |
| 4,008,249 | 2/1977 | Fischer et al. | 260/310 R |
| 4,033,986 | 7/1977 | Castenson et al. | 260/345.2 |
| 4,052,459 | 10/1977 | Malfroid | 260/592 |
| 4,065,502 | 12/1977 | MacKay et al. | 260/590 R |
| 4,072,498 | 2/1978 | Moon et al. | 71/92 |
| 4,096,184 | 6/1978 | Nakamura et al. | 260/561 N |
| 4,160,108 | 7/1979 | Shigeyasu et al. | 562/416 |
| 4,229,466 | 10/1980 | Miyazaki et al. | 424/279 |
| 4,260,775 | 4/1981 | Plath et al. | 548/362 |
| 4,323,692 | 4/1982 | Tanger | 560/65 |
| 4,327,104 | 4/1982 | Timmler et al. | 568/335 |
| 4,329,342 | 5/1982 | Heeres et al. | 568/335 |
| 4,339,599 | 7/1982 | Jongsma | 562/412 |
| 4,439,620 | 3/1984 | Klauke et al. | 562/493 |
| 4,485,254 | 11/1984 | Tanger | 560/21 |
| 4,752,326 | 6/1988 | Ohyama et al. | 71/92 |
| 4,820,845 | 4/1989 | Beck et al. | 548/378 |
| 4,895,984 | 1/1990 | Eggersdorfer et al. | 568/319 |
| 5,015,777 | 5/1991 | Chisolm et al. | 568/314 |
| 5,032,165 | 7/1991 | Miura et al. | 71/92 |
| 5,045,106 | 9/1991 | Moedritzer et al. | 71/92 |
| 5,053,517 | 10/1991 | Takigawa et al. | 548/376 |
| 5,068,449 | 11/1991 | Kumai et al. | 568/335 |
| 5,080,710 | 1/1992 | Rueb et al. | 71/96 |

(List continued on next page.)

FOREIGN PATENT DOCUMENTS

| | | | |
|---|---|---|---|
| 31200/89 | 9/1989 | Australia | C07D 413/10 |
| 0 020 964 | 1/1981 | European Pat. Off. | C07D 413/10 |
| 0 116 323 A1 | 8/1984 | European Pat. Off. | |
| 0 344 055 | 3/1989 | European Pat. Off. | C07D 413/10 |
| 0 361 114 | 4/1990 | European Pat. Off. | C07D 231/18 |
| 0 443 059 | 8/1991 | European Pat. Off. | C07D 231/18 |
| 0 619 946 | 10/1994 | European Pat. Off. | A01N 43/56 |
| 1 330 953 A | 5/1963 | France . | |
| 55-83751 | 6/1980 | Japan | C07D 231/12 |
| 62-77370 | 4/1987 | Japan | C07D 231/12 |
| 2-300173 | 12/1990 | Japan | A01N 43/56 |
| 3-47180 | 2/1991 | Japan | C07D 403/04 |
| 3-81275 | 4/1991 | Japan | C07D 403/04 |
| 3-93774 | 4/1991 | Japan | C07D 231/12 |
| 3-151367 | 6/1991 | Japan | C07D 231/20 |
| 3-72460 | 11/1991 | Japan . | |
| 70-02798 | 1/1995 | Japan | C07D 239/30 |
| 1 147 346 | 4/1969 | United Kingdom | C07C 63/26 |
| WO 90/09975 | 9/1990 | WIPO . | |
| WO 92/02509 | 2/1992 | WIPO | C07D 231/18 |
| WO 92/06962 | 4/1992 | WIPO . | |
| WO 94/00407 | 1/1994 | WIPO | C07B 41/08 |
| WO 95/32188 | 11/1995 | WIPO | C07D 231/20 |
| WO 96/02486 | 2/1996 | WIPO . | |
| WO 96/02515 | 2/1996 | WIPO | C07D 231/16 |
| WO 97/48668 | 3/1997 | WIPO . | |

OTHER PUBLICATIONS

Buu–Hoï, et al., "Carcinogenic Nitrogen Compounds. Part XIV. Friedel–Crafts Reactions with m– and p– Fluorotoluene," *J. Chem. Soc.*, pp. 386–388 (1953).
Gilman, et al., "Metalation of Aryl Fluorides in Tetrahydrofuran," *J. Org. Chem.*, vol. 22, pp. 1715–1716 (1957).
Gross, et al., *Chem. Ber.*, vol. 96, pp. 308–313 (1963).
Joshi, et al., "Studies in Fluorinated β–Diketones & Related Compounds: Part I—Syntheses of Some New Fluorinated β–Diketones & Their Copper Chelates," *Indian J. Chem.*, vol. 10, No. 5, pp. 485–488 (May 1972).
Osman, et al., "Synthesis of Unbranched 4–Alkylbenzalaldehydes," *Helv. Chim. Acta.*, vol. 65, pp. 2448–2449 (1982).
Pathak, et al., "Synthesis and Biological Activities of Some New 2–Arylamino–4–Fluoroarylthiazoles," *Pharmazie*, vol. 36, No. 5, pp. 331–332 (1981).
Rieche, et al., *Chem. Ber.*, vol. 93, pp. 88–94 (1960).
Scarpati, et al., *Synthetic Communications*, vol. 20, No. 17, pp. 2565–2572 (1990).

(List continued on next page.)

*Primary Examiner*—James H. Reamer
*Attorney, Agent, or Firm*—Grace L. Bonner; Arnold, White & Durkee

[57] ABSTRACT

The present invention relates to novel 4-halo-2-fluoro-5-alkylbenzoyl compounds and their methods of manufacture. These compounds are useful for the preparation of agricultural chemicals and medicines, particularly as intermediates for an active class of aryl-haloalkylpyrazole and aryl alkylsulfonylpyrazole herbicides.

7 Claims, No Drawings

U.S. PATENT DOCUMENTS

| | | | |
|---|---|---|---|
| 5,093,529 | 3/1992 | Schmand | 568/323 |
| 5,108,483 | 4/1992 | Kunisch et al. | 71/88 |
| 5,112,384 | 5/1992 | Miura et al. | 71/92 |
| 5,126,489 | 6/1992 | Kurek | 568/319 |
| 5,146,002 | 9/1992 | Yamada et al. | 568/337 |
| 5,155,258 | 10/1992 | Kamiya et al. | 562/429 |
| 5,156,668 | 10/1992 | Enomoto et al. | 71/92 |
| 5,281,571 | 1/1994 | Woodard et al. | 504/225 |
| 5,344,992 | 9/1994 | Drewes et al. | 568/314 |
| 5,347,054 | 9/1994 | Billeb et al. | 568/437 |
| 5,468,871 | 11/1995 | Ebel et al. | 548/373.1 |
| 5,489,571 | 2/1996 | Woodard et al. | 504/280 |
| 5,530,126 | 6/1996 | Woodard et al. | 544/52 |
| 5,532,416 | 7/1996 | Hamper et al. | 568/314 |
| 5,536,700 | 7/1996 | Woodard et al. | 504/128 |
| 5,545,609 | 8/1996 | Higashimura et al. | 504/282 |
| 5,587,485 | 12/1996 | Chupp et al. | 548/377.1 |
| 5,600,008 | 2/1997 | Hamper et al. | 568/314 |
| 5,600,016 | 2/1997 | Hamper et al. | 568/437 |
| 5,654,490 | 8/1997 | Hamper et al. | 568/437 |

OTHER PUBLICATIONS

Sharma, et al., "Synthesis and Antifungal Activity of Aryloxyacetyl Hydrazones of Fluoro Aralkyl/Diaryl Ketones," *J. Indian Chem. Soc.*, vol. 61, No. 7, pp. 644–646 (Jul. 1984).

Shingare, et al., "Synthesis of Some Sulfonamide Derivatives," *J. Indian Chem. Soc.*, vol. 54, No. 7, pp. 705–708 (Jul. 1977).

Araneo et al., "Hydroperoxides as Pseudohalides: Oxidation . . . Arylation of Acrylonitrile," *J. Chem. Soc. Chem. Commun.*, pp. 1399–1400 (1995).

Barlengua et al., "Synthesis of Halogenated . . . 4–Chloropyrazoles," *J. Heterocycl. Chem.*, 23(2), pp. 459–461 (1986).

Blackman et al., "Amathamide Alkaloids from the Marine Bryozoan Amatha Wilsoni Kirkpatrick," *Heterocycles*, 85, vol. 23 (11), pp. 2828–2833 (1985).

Brooks et al., "Gas Chromatographic Studies of Catecholamines, Tryptamines, and Other Biological Amines" *Analytical Chemistry*, vol. 36, No. 8, pp. 1540–1545 (1964).

Broxton et al., "Ring Bromination of Aryl . . . Hypobromous Acid," *J. Chem. Soc.*, Perkin Trans. 1, 74 (15), pp. 1769–1771 (1974).

Burger et al., "1,5–Diazabicyclo[3,3,0]octa–2,6–dien . . . 4,5–Diazaocta–1,3,5,7–tetraen Ein . . . Pyrazol–Synthesen," *Chemische–Berichte*, 112, pp. 2620–2630 (1979).

Chemical Abstract 91 (17):140839j (1979).
Chemical Abstract No. 92:57881s(1980).
Chemical Abstract No. 109:230773c(1988).
Chemical Abstract 110(11):95234f (1990).
Chemical Abstract 111:15098R (1989).
Chemical Abstract 114:164226b (1991).
Chemical Abstract 119:27827n (1993).
Chemical Abstract 119:71940 (1993).
Chemical Abstract 120:244818K (1994).
Chemical Abstract 122:265037 (1995).
Chemical Abstract 122:265364 (1995).
Chemical Abstract 70:114911 (1969).
Chemical Abstract 91:105689/15 (1979).
Chemical Abstract 97:72283V (1982).
Chemical Abstract 97:72285 (1982).
Chemical Abstract WO 89/02887A (1989).

Chen, Ted K., et al., "A Convenient Synthesis Of 2,3,5,6–TetrahalogenopyridinesAnd Of 3,5–Bis(alkylthio)pyridinesFrom 2,6–Diaminopyridine," *J.C.S. Chem. Comm.*, pp. 1139–1140 (1980).

Fieser, L. F., et al., "Reagents For Organic Synthesis," *John Wiley and Sons, Inc.*, p. 73 (1967).

Frank, et al., "A Modified Procedure for Acid–Catalyzed Esterification with Isopropanol," *Chromatographia*, vol. 12, No. 3, pp. 168–170 (Mar. 1979).

Frick, W. et al., "Critical Experimental Parameters in Gas Chromatographic–Mass Spectrometric Analysis of Oligopeptide Hydrolysates at the Picomol Level" *Analytical Chemistry*, vol. 49, No. 8, pp. 1241–1245 (1965).

Friedlaender et al., *Chemische Berichte*, vol. 47, pp. 3040–3052 (1914).

Gol'dfarb, Ya. L., et al., "New Method For Preparation Of 2–Bromothiophene," *Bulletin of the Academy of Sciences of the USSR Division of Chemical Science*, vol. 31, No. 10(2), pp. 2104–2105 (Oct. 1982).

Grimmett, M. Ross, "Halogenation Of Heterocycles: I. Five–Membered Rings," *Advances In Heterocyclic Chemistry*, vol. 57, pp. 291, 293–297, 336, 341–343 (1993).

Hartman et al., "Untersuchungen an Diazoverbindungen Und Arsden–Xx" *Phosphorics*, vol. 5, pp. 21–29 (1974) (w/English Abstract).

Houben–Weyl, "Carbonsäuren und Carbonsäure–Derivate," *Methoden der Organischen Chemie*, vol. E5, pp. 677–678 (1985).

Ingle, "Synthesis of Some New 3,5–Disubstituted–Pyrazoles", J. Indian Chem. Soc., p. 852, (1988).

Ishihara et al., "A New Effective . . . F–Alkyl Ketones," *Chem. Letters*, pp. 819–822 (1988).

Itahara, Toshio, et al., "ChloroperoxidaseCatalyzedHalogenationOfPyrimidineBases," *Chemistry Letters*, pp. 2311–2312 (1987).

Joshi et al., "Studies . . . Compounds IV," *J. Inorg. Nucl. Chem.*, 39, pp. 803–810 (1977).

Joshi et al., "Studies . . . Derivatives," *Indian J. Chem.*, 14B, pp. 1004–1006 (1976).

Karimi–Khoozani, et al., "Nitroimidazoles XI. Syntheses of Substituted (1–Methyl–5–Nitro–2–Imidazolyl) Pyrazoles," *Heterocycles*, vol. 38, No. 3, pp. 503–510 (1994).

Katritzky, "Advances in Heterocyclic Chemistry," *Academic Press*, vol. 6, pp. 358–361 (1966).

Kellogg, B. A., et al., "Base Catalyzed Hydrolysis And $^{18}O=C$ Exchange Of Ethyl And Isopropyl Toluoate in $H_2O$ and $D_2O$ Media. The Anionic Tetrahedral Intermediates Are Protonically Equilibrated," *J. Am. Chem. Soc.*, vol. 117, No. 6, pp. 1731–1735 (1995).

Kivinen, Antti, "Mechanisms Of Substitution At The COX Group," *The Chemistry Of Functional Groups*, pp. 177, 182–191 (1972).

Leung, et al., "Metabolism and Distribution of the Experimental Triazolone Herbicide F6285 [1–[2, 4–Dichloro–5–[N–(methylsulfonyl)amino]phenyl]–1, 4–dihydro–3–methyl–4–(difluoromethyl)–5H–triazol–5–one] in the Rat, Goat, and Hen, " J. Agric. Food Chem., vol. 39, pp. 1509–1514 (1991).

Morrison, et al., "Carboxylic Acids," *Organic Chemistry*, 5th Edition, p. 824. (1986).

Nakatsuka et al., "Methyl Group at 1–Position of Stabilized Indole as a Protective Group," *Heterocycles*, vol. 24, No. 10, pp. 2791–2792 (1986).

Texter–Boullet et al., "Pyrrole and Pyrazole Ring Closure in Heterogeneous Media," *Communications*, pp. 409–411 (May 1986).

Trujillo, John I., et al., "Facile Esterification Of Sulfonic Acids And Carboxylic Acids With Triethylorthoacetate," *Tetrahedron Letters*, vol. 34, No. 46, pp. 7355–7358 (1993).

BENZOYL DERIVATIVES AND SYNTHESIS THEREOF

RELATED APPLICATION

This application is a continuation of application Ser. No. 08/277,725, filed Jul. 20, 1994 now U.S. Pat. No. 5,532,416, which is a continuation-in-part of Ser. No. 08/169,285, filed Dec. 20, 1993, now U.S. Pat. No. 5,536,120, which is a continuation of Ser. No. 07/763,762, filed Sep. 25, 1991, now U.S. Pat. No. 5,281,571.

FIELD OF THE INVENTION

The present invention relates to novel benzoyl derivatives and their methods of manufacture. These compounds are useful for the preparation of agricultural chemicals and medicines and particularly, as intermediates for an active class of arylhaloalkylpyrazole and aryl alkylsulfonylpyrazole herbicides.

BACKGROUND OF THE INVENTION

In recent years it has been found that one class of active herbicides are the substituted phenylpyrazoles, the phenyl and pyrazole moieties of which contain a variety of substituents.

Methods of manufacturing these phenylpyrazoles commonly involve chemical conversions of one or more radicals substituted on the phenyl and/or pyrazole moieties, e.g., by halogenation, esterification, etc. It is also known to prepare these compounds from substituted acetophenones by interaction with various compounds, including various esters which contribute the desired substituent radical to the 5-position of the pyrazole radical via cyclization of an intermediate phenyl diketone. For example, various halo- and/or alkyl-substituted acetophenones have been reacted with (halo)acetic acid esters to produce the corresponding phenyl diketone which is cyclized with hydrazine to yield phenylpyrazoles substituted in the 5-position of the pyrazole radical with (halo)alkyl groups.

It has recently been disclosed that certain 3-substituted aryl-5-substituted pyrazoles are particularly useful for broadspectrum control of a variety of weeds at very low application rates in a number of agronomically important crops. The aryl group is typically the phenyl radical substituted with halogen, alkyl, alkoxy and ester groups, which substituents are also commonly found on the pyrazole moiety. Particularly effective within this class of compounds are esters of 2-chloro-5-(4-halo-1-methyl-5-(trifluoromethyl)-1H-pyrazol-3-yl)-4-fluorobenzoic acid. These particular compounds are most readily available from 2-fluoro-5-alkylacetophenones and their derivatives. The literature, however, does not provide methods of preparation of these intermediates or related compounds that could provide the desired pyrazolylbenzoic acids. Thus, there is a need in the art for the discovery of novel intermediates and for efficient methods for the preparation of these substituted arylpyrazole compounds.

The present invention describes intermediates useful for production of compounds within this new class of herbicides.

SUMMARY OF THE INVENTION

The present invention relates to a class of benzoyl derivatives of Formula I and synthesis methods therefor:

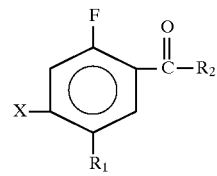

wherein X is H or a halogen atom, $R_1$ is a $C_{1-6}$ alkyl group optionally substituted with halogen or alkoxy or alkoxyalkyl having up to 6 carbon atoms; and $R_2$ is $C_{2-6}$ alkyl or $C_{1-6}$ haloalkyl or H, OH or —$CH_2COR_3$; wherein $R_3$ is a $C_{1-6}$ haloalkyl group.

A preferred subgenus of the benzoyl compounds in this invention are those according to Formula I wherein:

X is Cl or Br;

$R_1$ is methyl and $R_2$ is H, OH, halogen, methyl or —$CH_2COR_3$ wherein $R_3$ is $CF_3$, $CF_2Cl$ or $CF_2H$.

The most preferred species herein are those according to Formula I wherein X is chloro, $R_1$ is $CH_3$ and $R_2$ is —$CH_2COCF_3$.

As readily apparent to those skilled in the art, when $R_2$ in Formula I is hydrogen, the resulting compound (Formula IA below) is a substituted benzaldehyde; when $R_2$ is methyl (Formula IB below), the compound is a substituted acetophenone and when $R_2$ is the —$CH_2COR_3$ radical, the resulting compound is a substituted phenyldiketone (Formula ID below). All of these compounds have the substituted benzoyl radical as a common structural feature, hence, for simplicity and convenience herein all of these compounds will be referred to collectively as benzoyl derivatives.

To applicants' knowledge all of the substituted benzoyl derivatives herein are novel compounds, except the 4-chloro-2-fluoro-5-methyl acetophenone compounds, which is known in the art as an intermediate to make substituted phenyl ketoesters wherein the radical analogous to $R_3$ in the above Formula I is an alkoxy radical, but not a haloalkyl radical as herein. Moreover, said substituted phenylketoesters when cyclized with hydrazine yield substituted phenylpyrazolones wherein the pyrazole moiety is substituted on the carbon atoms only with O⇌OH moieties. (Japanese LOP Application (KOKAI) No. 3-72460.)

DETAILED DESCRIPTION OF THE INVENTION

Compounds of Formula I wherein $R_1$ is a methyl group and X is H or a halogen and $R_2$ is H (Formula IA) or methyl (Formula IB) are prepared from 2-substituted-4-fluorotoluenes of Formula II, which are known in the art.

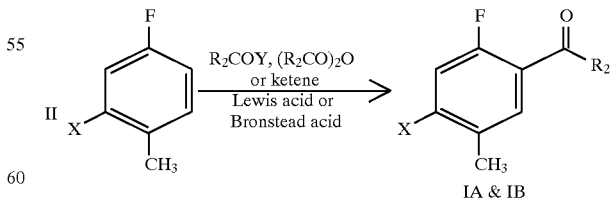

The 2-substituted-4-fluorotoluenes of Formula II can be acylated by either an acyl halide ($R_2$COY wherein Y is a halogen atom), an anhydride or a ketene ($CH_2CO$) in the presence of a Lewis acid or Bronstead acid at a temperature in the range of −50° C. to 200° C., preferably 0° C. to 100° C. The amount of acylating agent, an acyl halide, anhydride or ketene, can range from just greater than one molar equivalent to an excess, preferably from 1 to 2 molar equivalents relative to the fluorotoluene. The acylating catalyst may be a Lewis acid, such as $AlCl_3$, $TiCl_4$, $BF_3$, $SnCl_4$ or $FeCl_3$ or a Bronstead acid such as polyphosphoric acid, HF, $CF_3COOH$, $H_2SO_4$, etc. The amount of catalyst can be from less than 0.1 mole % to excesses greater than 100 mole % relative to the fluorotoluene. Any inert solvent may be used in this reaction that does not markedly hinder the reaction from proceeding or the reaction may be carried out neat. Preferred solvents include, but are not limited to, nitrobenzene, carbon disulfide organic acids or halogenated hydrocarbons. The reaction pressure is usually from 1 to 60 $kg/cm^2$, preferably from 1 to 10 $kg/cm^2$. The reaction period may be chosen from the range of a few minutes to several weeks depending on the amounts of reagents, reaction temperature, etc.

Compounds according to Formula I wherein $R_2$ is the hydroxy (OH) radical, i.e., benzoic acids according to Formula IC below, can be prepared, e.g., by the direct oxidation of the corresponding benzaldehyde or by a two-step procedure described below wherein $R_2$ is OH or H.

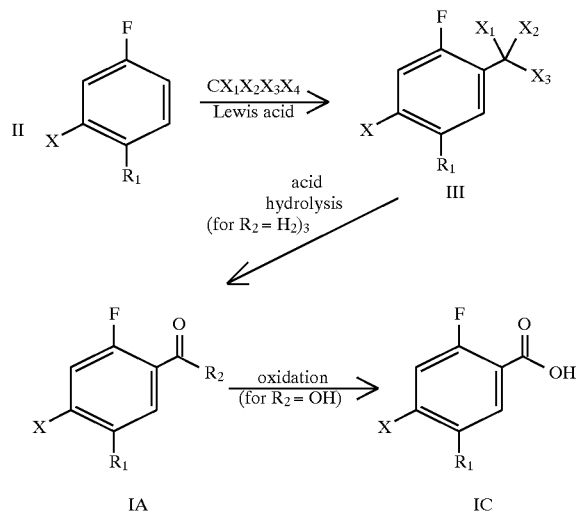

The compounds of Formula III above are prepared by alkylation of 2-substituted-4-fluoro-1-alkylbenzenes of Formula II with an alkylating agent $CX_1X_2X_3X_4$ in the presence of a Lewis acid. For the alkylating agent, $X_1$ and $X_2$ are independently halogens, $X_3$ is a halogen or hydrogen and $X_4$ is a halogen or (substituted)alkoxy substituent. Typical and preferred alkylating agents include, but are not limited to, 1,1-dichloromethyl methyl ether, carbon tetrachloride and carbon tetrabromide. The alkylating catalyst may be a Lewis acid, such as $AlCl_3$, $TiCl_4$, $BF_3$, $SnCl_4$ or $FeCl_3$ or a Bronstead acid such as polyphosphoric acid, HF, $CF_3COOH$, $H_2SO_4$, etc. The amount of catalyst can be from less than 0.1 mole % to excesses greater than 100 mole % relative to the fluorobenzene. Any inert solvent may be used in this reaction that does not markedly hinder the reaction from proceeding or the reaction may be carried out neat. Preferred solvents include, but are not limited to, nitrobenzene, carbon disulfide organic acids or halogenated hydrocarbons. The reaction pressure is usually from ambient pressure to 60 $kg/cm^2$, preferably from 0.5 to 10 $kg/cm^2$. The reaction period may be chosen from the range of a few minutes to several weeks depending on the amounts of reagents, reaction temperature, etc. Products are obtained by treatment of the reaction mixture with water and isolation of the product by standard methods. Often, the intermediate of Formula III is not isolated, but directly converted to the benzaldehyde compounds of Formula IA by acid hydrolysis, then if desired to benzoic acids by oxidation. Overall yields can be greatly improved by treatment of the crude product from the alkylation step with mineral acids, such as conc. $H_2SO_4$ or HCl to convert any geminal dichlorides or trichlorides to aldehydes and carboxylic acids, respectively. Isolation of compounds of Formula IA and IC can then be carried out in the usual manner.

As mentioned above, while benzoic acids of Formula IC can be obtained by a 2-step route from alkylation of the substituted toluene substrate with compounds such as carbon tetrachloride followed by hydrolysis, it is also possible to convert the Formula IA benzaldehydes directly to the benzoic acids of Formula IC by oxidation. Preferred oxidants include, but are not limited to, chromium oxide, chromium oxide in sulfuric acid, potassium permanganate, potassium dichromate, etc. Reaction temperature is in the range of −78° C. to the boiling point of the reaction mixture, preferably 0° C. to 100° C. The reaction period may be chosen from the range of a few minutes to several weeks depending on the amounts of reagents, reaction temperature, etc.

Compounds of Formula ID are prepared from compounds of Formula IB by reaction with $R_3COZ$ wherein Z is a $C_{1-6}$ alkoxy or $C_{6-8}$ aryloxy group or a halogen atom or by reaction with anhydride $(R_3CO)_2O$, where in both formulae, $R_3$ is $C_{1-6}$ haloalkyl.

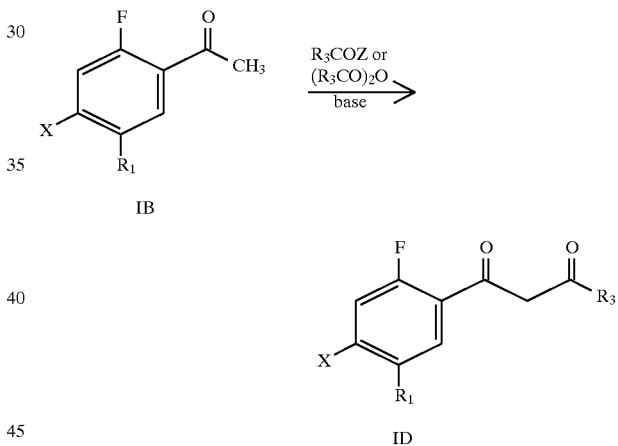

Thus, diketones of Formula ID can be prepared by treatment of 2-fluoro-4-(H or halogen)-5-alkylacetophenones with an ester, an anhydride or an acid halide in the presence of a base. Any suitable solvent or mixture of solvents can be employed; the preferred solvents are anhydrous ether, alcohols, dimethylsulfoxide, toluene, benzene, etc. The reaction is carried out in the presence of a base such as an alkali alkoxide, alkali amide or alkali hydride with the alkali alkoxides such as sodium methoxide being preferred. Reaction temperature is in the range of −100° C. to 200° C., preferably −78° C. to the reflux temperature of the solvent. The reaction period may be chosen from the range of a few minutes to several weeks depending on the amounts of reagents, reaction temperature, etc.

Compounds of Formula ID are meant to include all possible tautomers, such as enols and all possible salts wherein the cation is an alkali metal or other suitable organic or inorganic cationic species.

The compounds of Formula ID can be converted to pyrazolylbenzoyl esters useful as synthetic herbicides by the following reactions.

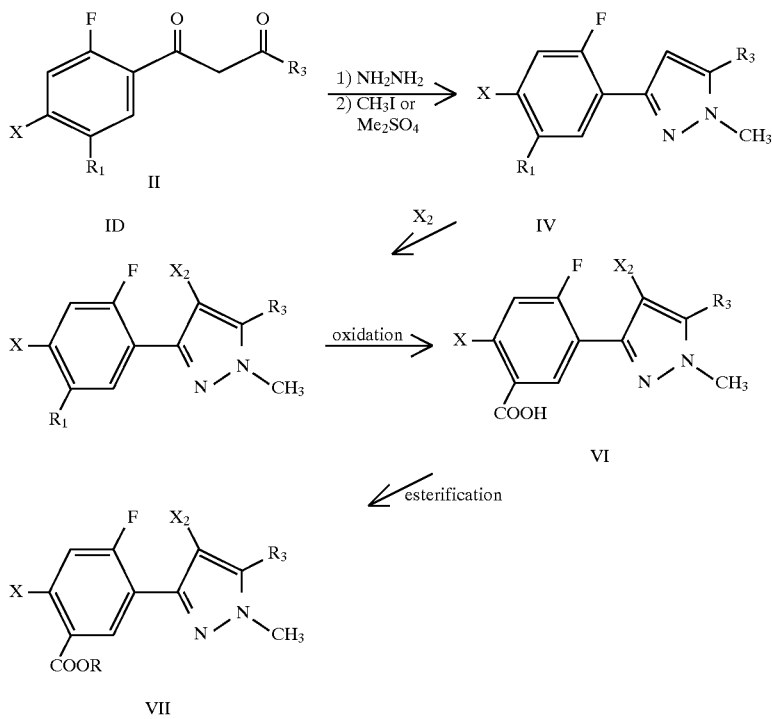

In the above formulae, $R_1$, $R_3$ and X are as previously defined for Formula I, $X_2$ is a halogen atom and R is a $C_{1-6}$ alkyl or substituted alkyl group, preferably those having $C_{1-4}$ carbon atoms.

The following examples describe specific working embodiments for the preparation of representative compounds according to this invention.

Examples 1–5 exemplify preparation of representative substituted phenyldiketones.

EXAMPLE 1

Preparation of 1-(4-Chloro-2-fluoro-5-methylphenyl)-4,4,4-trifluoro-1,3-butanedione A solution of 25.0 g of 1-(4-chloro-2-fluoro-5-methylphenyl)ethanone (see Example 6) and 23.9 ml of ethyl trifluoroacetoacetate in 50 ml of ether was prepared in a 500 ml flask equipped with a magnetic stirrer. The solution was cooled in an ice water bath and 31.4 ml of 25% sodium methoxide in methanol was added slowly such that the temperature did not exceed 10° C. The cooling bath was removed and the clear orange solution was allowed to stir at ambient temperature overnight. The reaction was poured onto ice with 100 ml of 10% HCl, and extracted with diethyl ether. The organic layer was washed with 5% HCl, dried with $MgSO_4$, filtered and concd in vacuo. The residue was dissolved in 200 ml of warm hexanes, dried, filtered and chilled. The resulting solid was filtered and air dried to afford 24.0 g (63% yield) of 1-(4-chloro-2-fluoro-5-methylphenyl)-4,4,4-trifluoro-1,3-butanedione as an off-white solid: mp 59°–60° C.;
$^1$H NMR ($CDCl_3$) δ14.9 (s, very broad, 1H), 7.78 (d, J=7 Hz, 1H), 7.14 (d, J=11 Hz, 1H), 6.60 (s, 1H), 2.33 (s, 3H).
Anal. Calc. for $C_{11}H_7O_2F_4Cl_1$: C,46.75; H,2.50.
Found: C,46.80; H,2.49.

Following substantially the same general procedure described in Example 1, the compounds of Examples 2–5 were prepared; these compounds are identified in Table 1, together with available physical properties.

TABLE 1

| EXAMPLE No. | X | $R_3$ | mp/Physical Properties |
|---|---|---|---|
| 2 | F | $CF_3$ | 38.5–40.0° C. |
| 3 | Br | $CF_3$ | 68–69° C. |
| 4 | Cl | $CF_2Cl$ | orange solid[1] |
| 5 | Cl | $CF_2H$ | 53–54° C. |

[1]NMR($CDCl_3$) δ 7.74(d, J=8Hz, 1H), 7.10(d, J=11Hz, 1H), 6.54(s, 1H), 2.29(s, 3H).

In Examples 6–10 below are described the preparation of representative 2-fluoro-4-(H or halo)-5-methylphenyl ketone compounds according to Formula I in which $R_2$ is an alkyl radical, i.e., compounds according to Formula IB.

EXAMPLE 6

Preparation of 1-(4-Chloro-2-fluoro-5-methyl-phenyl) ethanone.

A slurry of 22.9 g of 2-chloro-4-fluorotoluene and 45.8 g of aluminum trichloride was prepared in a 500 ml, mechanically stirred flask and treated with 18.7 g of acetyl chloride. An easily stirred slurry formed as the reaction temperature rose to 40°–50° C. Slow, steady gas evolution began. When this gas evolution ceased, the reaction was complete. The reaction mixture was treated with 100 ml of methylene chloride and the liquid decanted into an addition funnel. Ice was added to the residual solid until reaction ceased, ice water was added and the liquid from the addition funnel was added dropwise with cooling such that the temperature did not exceed 15° C. The organic layer was collected and washed with water, dried with $MgSO_4$, filtered and concd in vacuo. The residue was bulb-to-bulb distilled (bp=60° C. @ 0.5–0.05 mm) to afford 28.0 g (95%) of 1-(4-chloro-2-fluoro-5-methylphenyl)ethanone as a colorless oil (melts near room temperature): $\eta_{D23.0}$ 1.5317; $^1$H NMR ($CDCl_3$) $\delta$7.60 (d, J=8 Hz, 1H), 7.01 (d, J=14 Hz, 1H), 2.47–2.49 (m, 3H), 2.22 (s, 3H).

Anal. Calc. for $C_9H_8O_1F_1Cl_1$: C,57.93; H,4.32.

Found: C,57.78; H,4.27.

Following the same procedure described in Example 6, the compounds listed in Table 2 were also prepared and identified.

TABLE 2

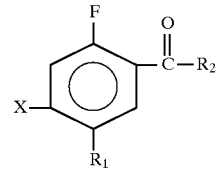

| EXAMPLE | X | $R_2$ | mp/refractive index |
|---|---|---|---|
| 7 | H | $CH_3$ | $\eta_D$ = 1.5063 @ 23° C.[1] |
| 8 | F | $CH_3$ | $\eta_D$ = 1.4905 @ 25° C. |
| 9 | Br | $CH_3$ | $\eta_D$ = 1.5523 @ 23° C. |
| 10 | Cl | $CH_2CH_3$ | 34.5° C. |

[1]Example 7 was obtained as a mixture of two isomers, i.e., 2-fluoro-5-methylacetophenone and 5-fluoro-2-methylacetophenone in a ratio of 85:15, the 2-fluoro isomer being the major product.

EXAMPLE 11

This example describes the preparation of compounds according to Formula I wherein $R_2$ is hydrogen; these are the 2-fluoro-4-chlorobenzaldehydes of Formula IA; in this example the prepared compound was 4-chloro-2-fluoro-5-methylbenzaldehyde.

To a stirred solution of 25 g (0.17 mole) of 2-chloro-4-fluorotoluene in 200 mL of methylene chloride was added 39 mL (0.35 mole) of titanium tetrachloride followed by the dropwise addition of 1,1-dichloromethyl methyl ether. The solution was kept at 0° C. for 4 hours, subsequently poured onto ice and extracted with ethyl acetate. The combined extracts were washed twice with brine, dried with $MgSO_4$ and concd. in vacuo. The resultant oil was diluted with 200 mL of sulfuric acid and stirred overnight at room temperature. This hydrolysis reaction mixture was poured onto ice, extracted with ethyl acetate, the combined extracts washed with sodium bicarbonate solution, dried with $MgSo_4$ and concd. to give 17.0 g (57%) of a white solid: mp 69° C. –70° C.; $^1$H NMR ($CDCl_3$) $\delta$2.41 (s, 3H), 7.24 (d, 1H), 7.75 (d, 1H), 10.31 (s, 1H).

Anal. Calcd for $C_8H_6O_1F_1Cl_1$: C, 55.68; H, 3.50

Found: C, 55.77; H, 3.51.

EXAMPLE 12

This example exemplifies the preparation of Formula I compounds wherein $R_2$ is OH; these are, of course, the intermediate substituted benzoic acid compounds of Formula IC.

This example describes the preparation of 4-chloro-2-fluoro-5-methylbenzoic acid by the direct oxidation of the corresponding precursor benzaldehyde.

To a solution of 219 g (1.3 mole) of 4-chloro-2-fluoro-5-methylbenzaldehyde (see Example 11) in 2 L of acetone cooled to 0° C. was added 487 mL (1.3 mole) of freshly prepared Jones' reagent dropwise; this reagent is a well-known oxidizing agent comprising a solution of chromic acid in $H_2SO_4$, 2.67 M. After addition was complete, the mixture was allowed to warm to room temperature and stirred for three hours. The mixture was added to 2 L of saturated brine, extracted twice with ethyl acetate and the combined extracts washed with 5% 30 aq. HCl, dried with $MgSO_4$ and concd. to afford 147 g (60%) of a white solid: mp 172° C.–173° C.; $^1$H NMR ($d^6$-DMSO) $\delta$2.32 (s, 3H), 7.49 (d, 1H, J=10 Hz), 7.83 (d, 1H, J=8 Hz), 13.35 (brs, 1H); $^{19}$F NMR ($d^6$-DMSO) $\delta$–111.8 (m, 1F).

The novel benzoyl derivatives of the present invention are useful as intermediates for the preparation or manufacture of gricultural chemicals and medicines, particularly the substituted phenylpyrazole type herbicides. These intermediates allow direct introduction of a 5'-alkyl substituent on the phenyl ring of the phenylpyrazole which can be converted to pyrazolylbenzoic acids and esters thereof.

As will be appreciated by those skilled in the art, various modifications of the invention described herein may be made without departing from the spirit and scope thereof.

We claim:

1. Compounds according to Formula I wherein

X is halogen;

$R_1$ is $C_{1-6}$ alkyl optionally substituted with halogen or alkoxy or alkoxyalkyl having up to 6 carbon atoms and $R_2$ is H, OH, $C_{2-6}$ alkyl or $C_{1-6}$ haloalkyl or $-CH_2COR_3$, wherein $R_3$ is $C_{1-6}$ haloalkyl.

2. Compounds according to claim 1 wherein X is chloro and $R_1$ is methyl.

3. Compounds according to claim 2 wherein $R_2$ is hydrogen.

4. Compounds according to claim 2 wherein $R_2$ is OH.

5. Compounds according to claim 2 wherein $R_2$ is $C_{2-6}$ alkyl or $C_{1-6}$ haloalkyl.

6. Compounds according to claim 2 wherein $R_2$ is $-CH_2COR_3$ and $R_3$ is $C_{1-6}$ haloalkyl.

7. Compounds according to claim 6 wherein $R_3$ is $-CF_3$.

* * * * *